United States Patent [19]

Marelli

[11] Patent Number: 5,431,155
[45] Date of Patent: Jul. 11, 1995

[54] SINGLE-DOSE NASAL DISPENSER FOR ATOMIZED LIQUID DRUGS

[75] Inventor: Andrea Marelli, Mi, Italy

[73] Assignee: Elettro Plastica S.p.A., Mi, Italy

[21] Appl. No.: 59,131

[22] Filed: May 10, 1993

[30] Foreign Application Priority Data

Jun. 3, 1992 [IT] Italy .................. MI92A1370
Dec. 15, 1992 [EP] European Pat. Off. .......... 92121293

[51] Int. Cl.⁶ .......................................... A61M 11/00
[52] U.S. Cl. .......................... 128/200.14; 128/200.22
[58] Field of Search ............ 128/200.14, 200.18, 128/200.22

[56] References Cited

U.S. PATENT DOCUMENTS

5,284,132 2/1994 Geier ............... 128/200.22

FOREIGN PATENT DOCUMENTS

0021123 1/1981 European Pat. Off. .
0201701 11/1986 European Pat. Off. .
0212188 3/1987 European Pat. Off. .
0311863 4/1989 European Pat. Off. .
0486894 5/1992 European Pat. Off. .
WO93/00172 1/1993 WIPO .

*Primary Examiner*—Edgar S. Burr
*Assistant Examiner*—Aaron J. Lewis
*Attorney, Agent, or Firm*—Oblon, Spivak, McClelland, Maier, & Neustadt

[57] ABSTRACT

The invention relates to a manually actuated nasal dispenser, suitable for dispensing a liquid single dose in atomized form retained in a chamber which is part of the dispenser. The liquid consisting of or containing a substance having pharmaceutical activity, for instance calcitonin. The nasal dispenser has a very simple structure, it assures a perfect seal and insulation of the liquid retained in it till the moment of its use, and it is made in such a way that the dispensing of the liquid in atomized form occurs only after at least a minimum pressure having a predetermined value has been given, thus avoiding droppings of the liquid outside of the dispenser discharging nozzle.

3 Claims, 1 Drawing Sheet

SINGLE-DOSE NASAL DISPENSER FOR ATOMIZED LIQUID DRUGS

BACKGROUND OF THE INVENTION

1. Field of the Invention

The invention relates to a manually actuable dispenser for dispensing dosed amounts of liquid drugs in atomized form.

2. Discussion of the Related Art

It is known that many drugs, for instance calcitonin, are nasally administered: since these drugs are extremely expensive and sometimes they can cause undesired side effects if they are sprayed into nose in exceeding doses, some devices are used for their application by which an exactly predetermined liquid amount, in a totally atomized form, can be dispensed, leaving the lowest residual possible of said liquid unused in said devices.

Indeed, it often happens that the known devices are not suitable for dispensing practically all the liquid substance therein retained, or that the dispensing occurs also at a relatively low pressure, with consequent dropping (and therefore loss) of said liquid outside of the dispensing nozzle of the nasal distributor, or further that the devices have a very complicated structure and therefore extremely expensive, to such an extent to suggest sometimes, at least in part, their re-use.

Devices of such a type are, for instance, described in the patents EP-B-0218840 corresponding to the U.S. Pat. No. 4,921,142 patent, and in the improvement of said last patent, depicted in the EP-A-0388651 and in the pCT/WO/91/13689 (PCT/EP91/00457 application) patents, besides that in the EP-A-0452728 patent.

All the above mentioned patents describe nasal dispensers having a rather complicated structure and therefore expensive, some of which, at the end of their use, keeping in their inside a remarkable amount of the liquid, others not assuring a sufficient seal and insulation of said liquid in the inside of the device during the storage, further, others allowing the liquid dispensing even at excessively low dispensing pressures, with consequent liquid dropping.

To simplify the structure and to therefore control the expenditures of such devices, the French patent FR-B-2625981 proposed a nasal dispensing device comprising a seat in which a piston, which is part of the device itself, extends, in said seat a cylindrical ampoule being insertable which holds the desired amount of the liquid: when said ampoule is inserted in the mentioned seat, the piston, which is part of the device, penetrates in the inside of the ampoule itself, thus allowing the expulsion of the liquid in atomized form when said ampoule is pushed inside its own seat.

SUMMARY OF THE INVENTION

The main purpose of the present invention is to provide for a nasal dispenser of the above cited type, comprising a container of a single dose of a liquid having pharmaceutical activity, manually actuable for dispensing practically totally such a dose of the liquid, at a dispensing pressure always higher than a minimum predetermined value.

Another purpose of the invention is to provide for a nasal dispenser of the above mentioned type which assures, before manually actuating said device, a perfect seal and insulation of the liquid therein contained, the dispenser having, besides, a very simple structure and being extremely cheap.

The above purposes are achieved by a manually actuated nasal dispenser for dispensing dosed amounts of atomized liquid drugs, comprising a first body having a cylindrical chamber for containing at least one liquid drug dose and a second body slidingly mounted on said first body and having a nozzle for drug dispensing, said first body having an elongated shape and delimiting said chamber which is open at one end of said first body itself whose other end has a seat for the resting of a finger of one hand, and said second body consisting of a hollow elongated element of rounded shape from which at least one shaped element externally extends for the resting of at least another finger of said hand, and into which a tubular wall extends to which a piston slidable within said chamber is integral, said nozzle being provided in said hollow element in correspondence of a free end thereof, characterized in that one end of an elongated cylindrical stem, is inserted and retained said stem extending beyond the free edge of said tubular wall and having its other end extending into said chamber, said piston comprising a tubular sleeve made of resiliently yielding material superimposed to said stem, one end portion of said sleeve being mounted and retained on said tubular wall while the other end portion of the same sleeve extends and is seal slidable in said chamber, the intermediate portion of said sleeve consisting of a continuous wall resiliently flexible from which at least one annular continuous rib projects towards the inside, said rib being resiliently pushed on said stem to seal on it in rest condition of the dispenser, at least one continuous passage being formed between the internal surface of said sleeve and respectively the external surface of said stem, such passage being open at its ends in correspondence of said nozzle and respectively of said chamber and being seal intercepted, in an intermediate position, by said rib protruding from said intermediate portion of said sleeve.

Conveniently, said first and second bodies have shaped portions and cooperating among them to prevent the free ends of said stem and of said sleeve from discharging from said chamber and retaining means are provided which can be snap-passed upon manual actuation of said dispenser for retaining said first and second bodies in the resting position preliminary to dispensing.

BRIEF DESCRIPTION OF THE DRAWINGS

A preferred embodiment of the invention shown by mere and non limiting example will be now described to make the structure and the features of the nasal dispenser according to the present invention clearer, reference being made to the accompanying drawing wherein.

DESCRIPTION OF THE PREFERRED EMBODIMENT

Figure 1:
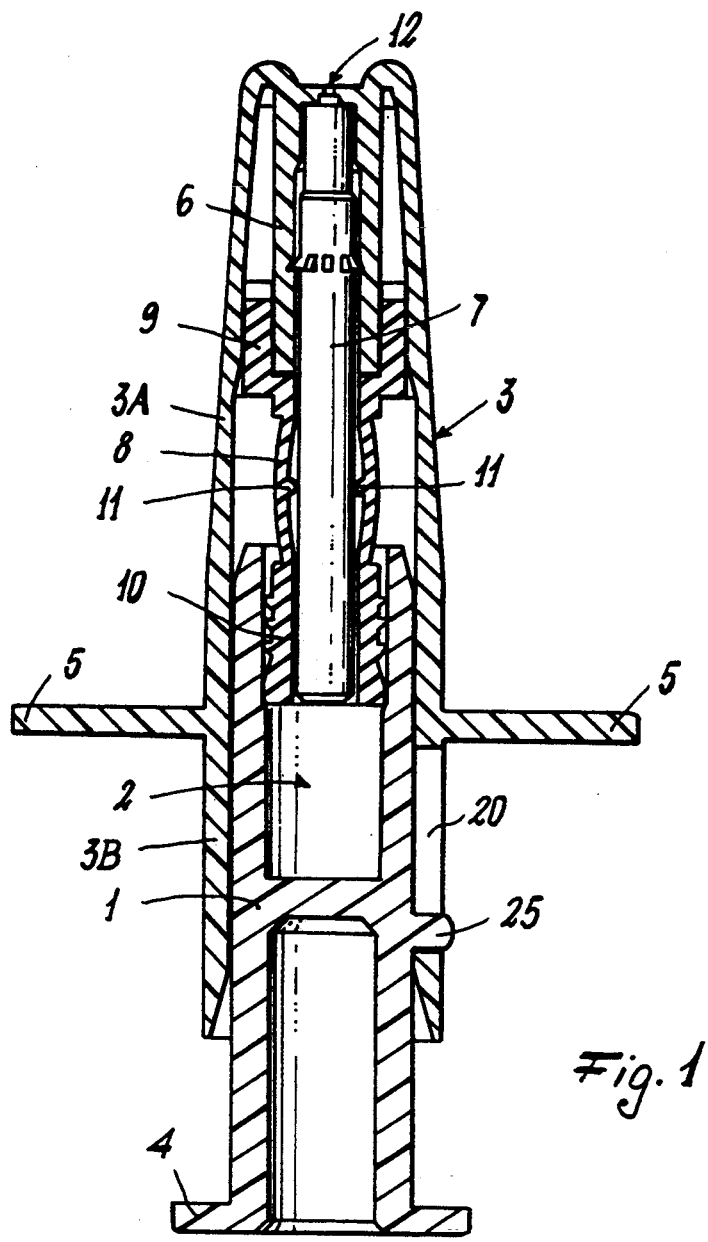
FIG. 1 is an enlarged cross-section, of a single dose nasal dispenser according to the invention.

The dispenser illustrated in the drawings comprises a first body 1 which defines a cylindrical chamber 2 suitable for containing a dose of a liquid drug, and a second body 3 slidably mounted on said first body 1 by manual action, such bodies being preferably made of plastics, by molding.

The first body 1 has an elongated shape and it delimits the above chamber 2 which is open in correspondence of the upper end (with respect to FIG. 1) of the body itself, whose lower end has a seat 4 for the thumb of one hand by which the dispenser is actuated.

The second body 3 consists of an elongated hollow element 3A having a rounded profile (as it can be clearly seen from FIG. 1) from whose lower end (with respect to FIG. 1) it externally protrudes a wing 5 whereon two fingers of a hand can lean, and whose thumb can lean on the seat 4, at the moment of the dispenser actuation: in the inside of the hollow element 3A, it extends a tubular wall 6, wherein it is inserted and retained the upper end of a cylindrical elongated stem 7 which extends beyond and under the lower edge of the tubular wall 6 and whose other end, namely the lower end of the stem 7, extends and is slidable into the chamber 2, as it can be clearly seen from FIG. 1.

The stem 7 is surrounded by a tubular sleeve 8, 9, 10 made of rubber or of other suitable resiliently yielding material. The portion of the sleeve upper end 9 is mounted and steadily retained on the lower end of the tubular wall 6, while the portion of the lower end 10 thereof is internal to the chamber 2 and it is seal slidable on the cylindrical surface of said chamber 2.

The intermediate portion 8 of the sleeve consists of a resiliently flexible continuous wall wherefrom it extends towards the inside a continuous annular rib 11 which is resiliently pushed on the stem 7, making a seal on it: consequently the intermediate portion 8 of the sleeve takes a "barrel" shape, namely its longitudinal sections are arch shaped, as it can be clearly seen from FIG. 1.

It can be noticed from the drawing that, among the external surface of the stem 7 and the internal surfaces of the sleeve 8, 9, 10 respectively, a continuous passage is delimited (not indicated with reference numbers in the drawing, but provided all around said stem) which is closed, at one of its intermediate positions, by the rib 11 which is kept pressed on the stem 7 by the resilient action of the portion 8 of the sleeve. The passage opens in correspondence of the upper end 3A of the body 3, where the discharge nozzle 12 is provided wherefrom the liquid drug in atomized form can be discharged.

The above continuous passage can be made for instance, by providing for one or more grooves in the lower portion and in the upper one of the stem 7 or providing a series of projections in the inside of the portions 9 and 10 of the sleeve.

A protecting cap (not represented in the drawing) can be mounted and snap-retained on the body 3, the cap having to be obviously removed before using the nasal dispenser.

Figure 2:
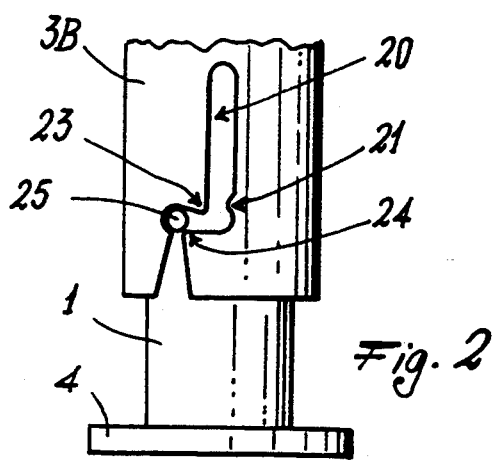
FIGS. 2 and 3 respectively represent, in frontal elevation, the end portion in two different blocked positions of the two dispenser components which are movable one upon the other.
Figure 3:
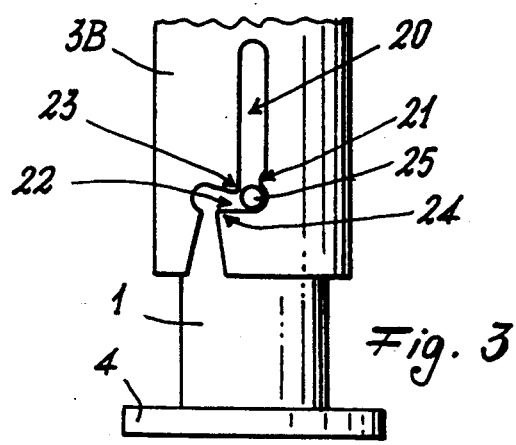

Reference can now be made also to FIGS. 2 and 3. It can be therefrom seen that in the lower part 3B of the body 3 there is one elongated and shaped window one of whose parts 20 extends longitudinally and has, near its lower portion, a relief 21 in correspondence of which there extends a substantially horizontal part 22 of the window delimited by two projections indicated by the numbers 23 and 25 respectively.

Radially towards the inside, from the body 1 it extends a stem 25 which is inserted and is slidable in the above mentioned window parts 22 and 20.

In the phase of preparing the dispenser, at first the body 1 is moved into the body 3, making the stem 25 slide in the window or slit at the lower end 3B of the body 3, till the stem 25 snap-passes beyond the relief 24, disposing itself and being retained in a tight manner in the first horizontal part 22 of the window, being therein blocked between the projections 23 and 24 (FIG. 2).

Obviously before mounting the body 3 on the body 1, the desired amount of the liquid drug is inserted into the chamber 2, being the drug destined to be dispensed by the dispenser.

It has to be noticed that when in the phase of the dispenser mounting, the stem 7 and the lower portion 10 of the sleeve 8, 9, 10 are moved into the chamber 2: the air therein present upon the surface of the liquid already introduced in said chamber 2, passes into the free space between the stem 7 and the portion 10 of the sleeve and causes a ball-like swelling of the portion 8 with the consequent lifting of the rib 11 away from the stem 7, in such a way that the air can be discharged towards the outside through the nozzle 12.

When the movement of introducing the stem and the sleeve is ceased, the pressure within the chamber lowers, reaching an equilibrium value, and the rib 11 resiliently and automatically makes back the seal on the surface of the stem 7.

This being made, the dispenser is ready for use.

It has to be noticed that in said conditions, unintentional dispensing of the liquid contained in the chamber 2 is not attained, the liquid remaining hermetically closed in the chamber itself, the stem 25 being retained in the position depicted in FIG. 2.

Supposition be now made wanting to use the dispenser: catching with two hands the body 3 and the lower part of the dispenser respectively, a rotation is caused, of the one in respect to the other, around their axis, in such a way that the stem 25 snap-passes the projection 23, disposing itself in the position shown in FIG. 3, wherein it is retained between the projection 23 and the projection 21.

The thumb of one hand is then leaned on the free end 4 of the body 1 and the forefinger and the medium finger of the same hand are leaned on the wings 5 exerting a high pressure which causes the snap-passing of the stem 25 beyond the holding edge 21, thus transmitting a pressure, having since from the start already a very high value to the liquid contained in the chamber 2.

The liquid after having passed in the open space between the stem and the facing surface of the portion 10 of the sleeve, causes the buckling or swelling towards the outside of the intermediate portion 8 of such sleeve and then the lifting of the annular rib 11 away from the surface of the stem 7, thus allowing the ejection of the liquid drug which passes from the chamber 2 beyond the annular rib 11, crosses the space delimited among the external surface of the stem and the internal surfaces of the sleeve and of the tubular element and discharges under pressure and in finely atomized form through the discharging nozzle 12, to be inhaled in the nostril of the nose of the utilizer.

It can be noticed that the push exerted on the lower surface of the portion 10 of the sleeve by the liquid under pressure, contributes to arch towards the outside the intermediate rounded portion 8 of the sleeve itself and helps therefore the lifting of the rib 11 away from the surface of the stem 7, thus favouring the expulsion of the liquid from the chamber 2.

The structure of the nasal dispenser is rather simple and the cost thereof is low as it can be easily understood by what it has been above described; the liquid in the chamber 2 remains completely isolated before the dispenser use and, during its utilization, the dispensing occurs at a very high pressure of a predetermined value, thus avoiding every form of dropping of the liquid outside of the discharging nozzle.

It is also evident that the structure of the dispenser can be carried out in different forms but equivalent to that one depicted in the drawings. For instance the retaining means of the stem 25, instead of being made up by the relief 21 and by the projections 23 and 24, can consist each of a thin wall or membrane carried out by molding together with the body 3, each of such walls or membranes being suitable to hold the stem 25 and being broken (in such a way that the stem 25 can snap-pass beyond it) when the stem 25 is pushed onto the membrane with a force sufficient to break the membrane itself.

What I claim is:

1. A manually actuated nasal dispenser for dispensing dosed amounts of atomized liquid drugs, the nasal dispenser comprising:

a first body having a cylindrical chamber for containing at least one liquid drug dose; and a second body slidingly mounted on said first body and having a nozzle for drug dispensing;

wherein:

said first body has an elongated shape and delimits said chamber which is open at a first end of said first body, a second end of said first body having a seat for resting a finger of one hand;

said second body comprises a hollow elongated element having a rounded shape from which at least one shaped element externally extends for resting at least another finger of said hand, a tubular wall extending into said hollow elongated element, a piston being mounted on said tubular wall and being slidable within said chamber, said nozzle being provided at a free end of said hollow elongated element;

a first end of an elongated cylindrical stem is inserted and retained within said tubular wall, a second end of said elongated cylindrical stem extending beyond a free edge of said tubular wall and into said chamber;

said piston comprises a tubular sleeve made of resiliently yielding material superimposed to said stem, a first end portion of said tubular sleeve being mounted and retained on said tubular wall, a second end portion of said tubular sleeve extending to said chamber and being seal slidable in said chamber, and an intermediate portion of said tubular sleeve comprising a continuous wall resiliently flexible from which at least one annular continuous rib projects in an inside direction toward said stem, said rib being resiliently pushed on said stem to seal on said stem in a rest condition of the dispenser; and at least one continuous passage is formed between an internal surface of said tubular sleeve and respectively an external surface of said stem, said passage being open at its ends in correspondence of said nozzle and respectively of said chamber and being seal intercepted, in an intermediate position, by said rib protruding from said intermediate portion of said sleeve;

wherein said rib is movable away from the stem when a pressure of liquid in said continuous passage is greater than a predetermined pressure and acts on said sleeve to move said intermediate portion of said sleeve in a direction away from said stem.

2. A nasal dispenser according to claim 1, wherein said first and said second bodies have shaped portions which cooperate among themselves to prevent free ends of said stem from discharging from said chamber.

3. A nasal dispenser according to one of claims 1 or 2, wherein retaining means are provided which can be passed upon manual actuation of said dispenser for retaining said first and second bodies in the resting position preliminary to dispensing.

* * * * *